US012033730B2

(12) United States Patent
Reumann et al.

(10) Patent No.: US 12,033,730 B2
(45) Date of Patent: Jul. 9, 2024

(54) MODEL AUGMENTED MEDICAL CODING

(71) Applicant: INTERNATIONAL BUSINESS MACHINES CORPORATION, Armonk, NY (US)

(72) Inventors: Matthias Reumann, Herrenberg (DE); Andrea Giovannini, Zurich (CH)

(73) Assignee: INTERNATIONAL BUSINESS MACHINES CORPORATION

(*) Notice: Subject to any disclaimer, the term of this patent is extended or adjusted under 35 U.S.C. 154(b) by 206 days.

(21) Appl. No.: 16/848,072

(22) Filed: Apr. 14, 2020

(65) Prior Publication Data
US 2021/0319859 A1 Oct. 14, 2021

(51) Int. Cl.
*G16H 10/60* (2018.01)
*G06F 40/40* (2020.01)
*G16H 15/00* (2018.01)
*G16H 50/20* (2018.01)

(52) U.S. Cl.
CPC ............. *G16H 10/60* (2018.01); *G06F 40/40* (2020.01); *G16H 15/00* (2018.01); *G16H 50/20* (2018.01)

(58) Field of Classification Search
CPC ........ G16H 10/60; G16H 50/20; G16H 15/00; G06F 40/40; G06F 40/279
See application file for complete search history.

(56) References Cited

U.S. PATENT DOCUMENTS

| 2010/0076780 A1 | 3/2010 | Mahesh | |
| 2014/0365242 A1* | 12/2014 | Neff | G16H 10/60 705/3 |
| 2015/0379241 A1* | 12/2015 | Furst | G06F 40/247 705/3 |
| 2016/0299577 A1 | 10/2016 | Trau | |
| 2017/0235887 A1 | 8/2017 | Cox | |
| 2018/0098737 A1 | 4/2018 | Villazón-Terrazas et al. | |
| 2019/0057083 A1 | 2/2019 | Karres | |

(Continued)

FOREIGN PATENT DOCUMENTS

| CN | 10927306 A | 1/2019 |
| CN | 109273062 A | 1/2019 |
| IN | 201741021746 A | 7/2017 |

OTHER PUBLICATIONS

IBM, List of IBM Patents or Patent Applications Treated as Related, Appendix P, dated May 6, 2020, 2 pages.

(Continued)

*Primary Examiner* — Gregory D. Moseley
(74) *Attorney, Agent, or Firm* — Lily Neff (57) ABSTRACT

The exemplary embodiments disclose a system and method, a computer program product, and a computer system for assigning medical codes. The exemplary embodiments may include receiving a medical record in machine-readable text-form, wherein the medical record comprises at least one treatment, converting a portion of the medical record into a determined first medical code of a first length, querying a knowledge graph comprising medical records and a coding catalog for a second medical code of higher order than the first medical code, wherein the second medical code relates to the first medical code, and searching evidence in the medical record for the second medical code by comparing at least a portion of clear text relating to the second medical code with the medical record.

19 Claims, 7 Drawing Sheets

(56) References Cited

U.S. PATENT DOCUMENTS

| | | |
|---|---|---|
| 2020/0012930 A1 | 1/2020 | Kumar |
| 2020/0051694 A1* | 2/2020 | Goldberg ............... G16H 50/20 |
| 2020/0118682 A1* | 4/2020 | Villazón-Terrazas ....................... G06N 20/00 |
| 2020/0227147 A1 | 7/2020 | Raddatz |

OTHER PUBLICATIONS

Pending U.S. Appl. No. 16/848,029, filed Apr. 14, 2020, entitled: "Assigning Medical Codings", pp. 1-53.

Bharadwaj, "Artificial Intelligence for Medical Billing and Coding",https://emerj.com/ai-sector-overviews/artificial-intelligence-medical-billing-coding/, Nov. 22, 2019, pp. 1-3.

Mell et al., "The NIST Definition of Cloud Computing", National Institute of Standards and Technology, Special Publication 800-145, Sep. 2011, pp. 1-7.

Ning et al., "A hierarchical method to automatically encode Chinese diagnoses through semantic similarity estimation", https://www.ncbi.nlm.nih.gov/pmc/articles/PMC4778321/, Mar. 3, 2016, pp. 1-22.

Xie et al., "A Neural Architecture for Automated ICD Coding", https://www.aclweb.org/anthology/P18-1098/, Jul. 2018, pp. 1066-1076.

Escobar-Vega L.M., Zaldfvar-Carrillo V.H., Villalon-Turrubiates I. (2018) Comparative Analysis and Implementation of Semantic-Based Classifiers. MICAI 2018. Lecture Notes in Computer Science, vol. 11289. Springer, Cham. https://doi.org/10.1007/ 978-3-030-04497-8_7 (Year: 2018).

* cited by examiner

MODEL AUGMENTED MEDICAL CODING

BACKGROUND

The invention relates generally to medical coding, and more specifically, to a computer-implemented method for augmenting medical coding. The invention relates further to a related system for augmenting medical coding, and a computer program product.

National and private healthcare systems around the world are supporting increasingly complex and expensive treatments. In any case, the insurance companies bear the burden of paying the amount paid to hospitals and doctors. Technically, however, there is no closed information supply chain from diagnosis through one or more treatments, which are usually part of a frequently handwritten medical record, to insurance companies.

Natural language processing (NLP) has been used to try to automate medical coding. The medical codes are typically organized hierarchically, i.e., as a sequence of characters comprising a main code and a respective sub-code. Although NLP technology may help with identifying some main codes, it often lacks accuracy to gain the more detailed sub-code. This is due to lack of data to train the NLP engine, and lack of context beyond sentence and/or paragraphs that the NLP engine looks at. In addition, individual hospitals and/or individual doctors may have their own abbreviations for specific treatments.

SUMMARY

The exemplary embodiments disclose a system and method, a computer program product, and a computer system for assigning medical codes. The exemplary embodiments may include receiving a medical record in machine-readable text-form, wherein the medical record comprises at least one treatment, converting a portion of the medical record into a determined first medical code of a first length, querying a knowledge graph comprising medical records and a coding catalog for a second medical code of higher order than the first medical code, wherein the second medical code relates to the first medical code, and searching evidence in the medical record for the second medical code by comparing at least a portion of clear text relating to the second medical code with the medical record.

BRIEF DESCRIPTION OF THE SEVERAL VIEWS OF THE DRAWINGS

It should be noted that embodiments of the invention are described with reference to different subject-matters. In particular, some embodiments are described with reference to method type claims, whereas other embodiments are described with reference to apparatus type claims. However, a person skilled in the art will gather from the above and the following description that, unless otherwise notified, in addition to any combination of features belonging to one type of subject-matter, also any combination between features relating to different subject-matters, in particular, between features of the method type claims, and features of the apparatus type claims, is considered as to be disclosed within this document.

The following detailed description, given by way of example and not intended to limit the exemplary embodiments solely thereto, will best be appreciated in conjunction with the accompanying drawings, in which.

The drawings are not necessarily to scale. The drawings are merely schematic representations, not intended to portray specific parameters of the exemplary embodiments. The drawings are intended to depict only typical exemplary embodiments. In the drawings, like numbering represents like elements.

DETAILED DESCRIPTION OF THE SEVERAL VIEWS OF THE DRAWINGS

According to one aspect of the present invention, a computer-implemented method for augmenting medical coding may be provided. The method may comprise receiving a medical record in machine-readable text-form comprising at least one treatment, converting a portion of the medical record into a determined medical code, querying a knowledge graph comprising medical records and a coding catalog for a medical code of higher order than the medical code of the first length relating to the determined medical code, and searching evidence for a medical code of higher order in the medical record by comparing at least a portion of clear text relating to a medical code of higher order with the medical record.

According to another aspect of the present invention, a system for augmenting medical coding may be provided. The coding system may comprise receiving means adapted for receiving a medical record in machine-readable text-form comprising at least one treatment, conversion means adapted for converting a portion of the medical record into a determined medical code of a first length, query means adapted for querying a knowledge graph comprising medical records and a coding catalog for a medical code of higher order than the medical code of the first length relating to the determined medical code, and search means adapted for searching evidence for a medical code of higher order in the medical record by comparing at least a portion of clear text relating to a medical code of higher order with the medical record.

The proposed computer-implemented method for augmenting medical coding may offer multiple advantages, technical effects, contributions and/or improvements:

Essentially, the proposed concept in form of the method, the system and the computer program product may allow a more precise determination of medical codes instead of only recognizing medical main codes of coding catalogs—e.g., only the three first characters—e.g., in handwritten medical records. OCR (optical character recognition) techniques and enhanced context analysis based on NLP may be used to determine in a two-step process also subcodes in the medical record that may otherwise not have been determinable. The trick may be requesting from a knowledge graph comprising medical coding catalogs as well as historic medical records with a correct determined medical coding in order to receive back a list of medical codes of a second length—i.e., the three-letter main code as well as a fourth and/or fifth character of the medical code, i.e., also the subcode—in order to have a much more precise description of the treatment or medical procedure applied to the patient.

The system can not only give back a proposed code to a user but may also deliver an estimation of a probability for the correctness—i.e., an evidence value—of the determined medical code. This may make life of human medical coders much easier because they get a clear guidance of how good the determined medical code is. It may be mentioned in this context that the notion of "medical code of higher order" may relate to a medical code having more characters, i.e., being more precise in terms of treatments and procedures, i.e., the medical subcode in contrast to the medical main code.

Additionally, the proposed system may also be able to learn from past coding decisions confirmed by a human user. The evidence found in the medical record in form of unknown expressions of abbreviations or other indicators may be used to expand and enhance the existing ontology of the used NLP system by integrating it into the ontology.

A combination of different machine-learning methods and/or systems may be used for enabling a relationship building between diagnosis codes and procedural codes. Firstly, handwritten medical records may be scanned and treated with OCR techniques in order to identify diagnosis codes. This process may be supported by NLP (natural language processing) techniques in order to isolate the medical codes from the context it is embedded in.

Furthermore, a knowledge graph may be used, in which information from a plurality of sources may be stored, to build a complex network of nodes and relationships, thereby delivering a sorted list of potential paths of medical diagnosis codes and related procedural codes—in particular, main and/or secondary diagnosis codes, as well as, main procedure codes, as well as, secondary procedure codes—as a result of a query. Thereby, the sorting of the list may be influenced by those medical cases with which the knowledge graph has been constructed. This may be hospital specific and/or insurance specific, depending on the medical records, the knowledge graph has been built with. In addition to the ground truth of past real medical cases and their related and existing medical coding, also complete catalogs of diagnosis codes and treatment procedure codes of different sources may be used as further input to the knowledge graph. Moreover, also rule of thumb guidelines—like the DRG handbook—may be used to enhance the content of the knowledge graph and qualify the edges, i.e., assign attributes to the edges of the knowledge graph.

Furthermore, the already mentioned NLP system or another, second NLP system trained according to different expressions and interdependencies between expressions may be used in order to verify records of the output of the query to the knowledge graph (the ranked list) in order to identify specific evidence in the medical records to confirm (or not) an output of the query—i.e., the ranks in the list—to the knowledge graph. According to the evidence value, the ranks in the list may also be changed such that the most probable relationships between diagnosis codes and procedure codes may be at the beginning of the list. This may enhance the speed with which the second partial process—in particular, finding evidence in the medical record for a medical subcode in the medical records.

In the following, additional embodiments of the inventive concept—applicable to the method as well as to the related system—will be described.

According to a useful embodiment, the method may also comprise, before the step of receiving a medical record in text-form, converting the medical record into the machine-readable text-form by optical character recognition. This may allow a conversion from often handwritten medical records as part of medical staff notes. The medical staff notes may be digitized by, e.g., a camera or a scanner and may then be fed to an optical character recognition system in order to extract characters, words and/or phrases.

According to one advantageous embodiment of the method, the step of searching evidence for a medical code of higher order may also comprise determining a confidence score for the medical code of higher order (i.e., the medical subcode), in particular, for the medical code of higher order being present or mentioned in the content of the medical record. This may be achieved even if the medical record may comprise abbreviations and/or a doctor-specific code.

According to another advantageous embodiment, the method may also comprise displaying the medical code of higher order—optionally together with the medical record—displaying the determined confidence score (i.e., the medical subcode), and receiving a confirmation signal—typically from a user, i.e., a specialist in medical coding—for replacing the determined medical code by the medical code of higher order. Thus, a more precise medical coding may be achieved by (i) a machine driven process and (ii) a final human decision (confirmation or denial).

According to an additional useful embodiment of the method, the medical record may comprise a surgery record and/or a discharge record for a patient. These events may typically represent the trigger points for payments.

According to one permissive embodiment of the method, the determined medical code may be an ICD-10 code (International Classification of Diseases, version 10) or an OPS code (Operations and Procedure code) or a CHOP code (Swiss Operations and Procedure). However, the proposed concept may be applied together with any medical procedure code or even with other classification systems based on hand-written records.

According to another useful embodiment of the method, the medical code of the first length may comprise three characters—i.e., a main code—and/or the medical code of higher order may comprise four or five characters, i.e., the subcode. As an example, the three-character code may indicate that a leg bone was broken and the two additional letters and/or characters may indicate which bone exactly was broken in which way. Thus, the medical code of higher order may allow a more precise categorization of the treatment required and the cost to be paid by the insurance company or the patient.

According to one further advantageous embodiment of the method, querying a knowledge graph may result in a list of medical codes of higher order. This may open up the option for trying to find or determine a confirmation or evidence in the medical records by turning back to the medical record with this list and trying to determine a confidence score for each one of the list of medical codes of higher order. The list may be generated using a knowledge graph comprising the hierarchical organization of the chosen medical coding scheme.

According to an additionally advantageous embodiment of the method, converting a portion of the medical record into a determined medical code or the searching for evidence for a medical code of higher order in the medical record may comprise the usage of a natural language processing system. Hence, the natural language processing system may be used for a first determination of the "short" medical code (i.e., the main code), and also for the second part of the process in which a second look is taken at the medical record in order to find evidence for at least one of the elements in the list provided.

According to a further advanced embodiment, the method may also comprise including a confirmed or approved medical code of higher order into an ontology used by the natural language processing system. This may expand the underlying set of directories and their related relations in the knowledge graph in order to "learn on the fly", i.e., allowing better and better medical code classifications the more often the proposed concept is used in daily operations.

According to another further enhanced embodiment, the method may also comprise querying the knowledge graph comprising the medical records—in particular historical medical records—and the coding catalog for a medical code of equal or lower order than the medical code of the first length relating to the determined medical code, and searching evidence for another medical code of equal or lower order in the current medical record by comparing at least a portion of clear text relating to a medical code of equal or lower order with said medical record.

Thus, according to this embodiment version, it cannot only be searched for a medical record unveiling more medical details (as the longer codes do) but it may also be searched for evidence for one or more medical codes of the same length which may deliver the same medical detail as the current medical code and which may be related. In an example, in the knowledge base in the historic medical records, certain medical codes of the same length may be related. If it may be determined that, e.g., in 70%—or any other threshold value—of all historic cases two medical codes may be mentioned in a medical record or as part of the already coded medical codes based on the related medical record, it may be searched with priority for the related medical code in the selected medical records because the probability to determine a relationship may be enhanced.

This way, a higher number of treatments and procedures may be identified—i.e., determined—in the current medical code.

Also here, a plurality of medical catalogs may be queried in the knowledge base.

According to another further enhanced embodiment of the method, the medical records in the knowledge graph may comprise medical codes associated with a main diagnosis and a secondary diagnosis, wherein the main diagnosis and the secondary diagnosis may be nodes in the knowledge graph, wherein an association may be represented as an edge between the medical code and the main and/or secondary diagnosis code, and wherein the query to the knowledge graph also result in a likelihood of the association of the medical code of the received medical record with the main and/or secondary diagnosis. Actually, the likelihood may be derived from a count of a number of associations per medical records.

This additional feature may further improve the likelihood of catching all relevant medical codes in the available information, i.e., from the current medical records, as well as from knowledge assets from history medical records in the knowledge base.

Furthermore, embodiments may take the form of a related computer program product, accessible from a computer-usable or computer-readable medium providing program code for use, by, or in connection, with a computer or any instruction execution system. For the purpose of this description, a computer-usable or computer-readable medium may be any apparatus that may contain means for storing, communicating, propagating or transporting the program for use, by, or in connection, with the instruction execution system, apparatus, or device.

In the context of this description, the following conventions, terms and/or expressions may be used:

The term 'augmenting medical coding' may denote a process in which medical codes may be assigned to treatments and procedures for which information may only be available in the form of medical records in text-form. The medical coding may be made much more precise by the augmented medical coding if compared to known technologies.

The term 'medical coding' may denote a process of assigning appropriate medical codes to medical terms in patient records. Additionally, medical coding may also be directed to assigning treatment codes of one or more medical treatments relating to a medical diagnosis code.

The term 'medical record' may denote an entry in a patient's file, wherein an individual record relates to one or more diagnoses and optionally also to medical treatments (and/or procedures). Medical records are still very often only available in hand-written forms. Another hurdle is that hospital specific terms are often used so that it is technically difficult to bridge the gap from individual hospitals with "local diagnoses and local treatments" to insurance companies. In case, the handwritten forms of the medical records have been "electronified" they are typically available in PDF (portable document format) form or as simple digital image. The access to a specific medical record may be performed by using the caseID (case identifier). A medical record may comprise one or more main codes and a plurality of sub-codes.

The term 'diagnosis code' may denote an entry in a standardized domain specific code table for medical diagnoses. A typical example is the ICD-10 code (International Classification of Diseases) or, on the other side, the medical treatment code system, namely the procedure code system(s).

The term 'procedure code' may denote one of a catalog of standardized medical treatments. One example of such a catalog, often used in Germany, is denoted as OPS (operations and procedure code); another one is CHOP, the Swiss catalog of operations and procedures. Other countries may have other catalogs in their respective medical systems which may also be used with the here proposed concept. Additionally, in this context, the term 'DRG handbook' may be defined: diagnosis related groups. Groups may denote groups of procedures relatable to a specific diagnosis. However, there is not a direct 1:1 relationship between a medical diagnosis and one or more related procedures. The medical world is much more complex, treatments change over time and may be hospital and/or doctor specific, and may underlie regional and medical school specific variations.

The term 'case identifiers'—in short caseID—may denote a unique code instrumental for identifying a specific diagnosis for a specific patient. The case identifier may represent the non-interchangeable code identifying a specific patient, a diagnosis time, the diagnosis, and optionally prescribed medical procedures.

The term 'knowledge graph' may denote, in a broad sense, a database for storing information of different topics and dynamically relating single expressions to each other. Knowledge graphs may be well suited for finding specific information and relating different terms/expressions to each other. For that, often distance measures are used between terms stored in the knowledge graph. Typically, expressions or terms of facts are stored in 'nodes' in a knowledge graph, while connections between individual ones of the nodes are termed 'edges'. These edges may also have attributes, e.g., describing the relationship between the nodes an edge may be connected to. In other cases, the edges may carry weights expressing a relationship strength between the connected nodes. A small example is described below in the context of FIG. 2.

The term 'optical character recognition'—abbreviated as OCR—may denote a technique to convert hand-written letters or expressions into a machine-readable form. For this, image recognition techniques may be used which may be supported by natural processing language (NLP) systems and may be supported by a machine learning system being trained for recognizing content in digital images and also for classifying terms and expressions in the medical records, as well as dependencies and typical sequences of expressions. Also, other machine-learning techniques, like neuronal networks, may be supportive for the here proposed concept.

The term 'machine-readable text-form' may denote a characteristic of a file comprising characters which are coded according to a known coding scheme, e.g., ASCII text (American Standard code for information exchange).

The term 'treatment' may denote a medical procedure applied to a patient.

The term 'portion of the medical record' may denote a portion of a text of the medical record comprising an indication of a specific medical code, i.e. main code or subcode. E.g., the portion of the text may be "broken right upper arm". This may related to, e.g., the IDC-10 code T10.

The term 'first length' may denote a length of e.g., three characters or digits denoting a higher level medical code.

The term 'coding catalog' may denote a list of medical codes and related treatments and/or procedures.

The term 'medical code of higher order' may denote a medical code with more digits than the medical code of the first length. If the length comprises the digits, the medical code of higher order comprises four or five digits or characters.

The term 'evidence for a medical code of higher order' may denote that an expression in the medical record relates to an expression or a synonym on abbreviation found in the knowledge graph during the query for the medical code of higher order. Hence, the natural language processing system receives as input value the medical code of higher order and searches the medical record for expressions that relate to the medical code of higher order. For this, it uses an ontology related to the NLP system.

The term 'confidence score' may denote a probability value for having determined a correct medical code of higher order relating to the text in the medical record. The higher the confidence core value—i.e., the evidence value—is, the more probable is a correct determination of a medical code of the higher order.

The term 'ICD-10 code' may denote a combination of letters and numbers according to the international classification of diseases. The number "10" may indicate the 10$^{th}$ version. However, the proposed concept may also be applicable for other versions of other medical code systems.

The term 'OPS code' may denote a code catalog often used in Germany. It denotes the operations of the procedure code catalog. Additionally, the term 'CHOP code' may denote the Swiss catalog of operations and procedures.

The term 'ontology' may denote a set of dictionaries and expressions including their associated relations that are used in the process determining the underlying and a piece system.

In the following, a detailed description of the figures will be given. All instructions in the figures are schematic. Firstly, a block diagram of an embodiment of the inventive computer-implemented method for augmenting medical coding is given. Afterwards, further embodiments, as well as embodiments of the system for augmenting medical coding, will be described.

Figure 1:
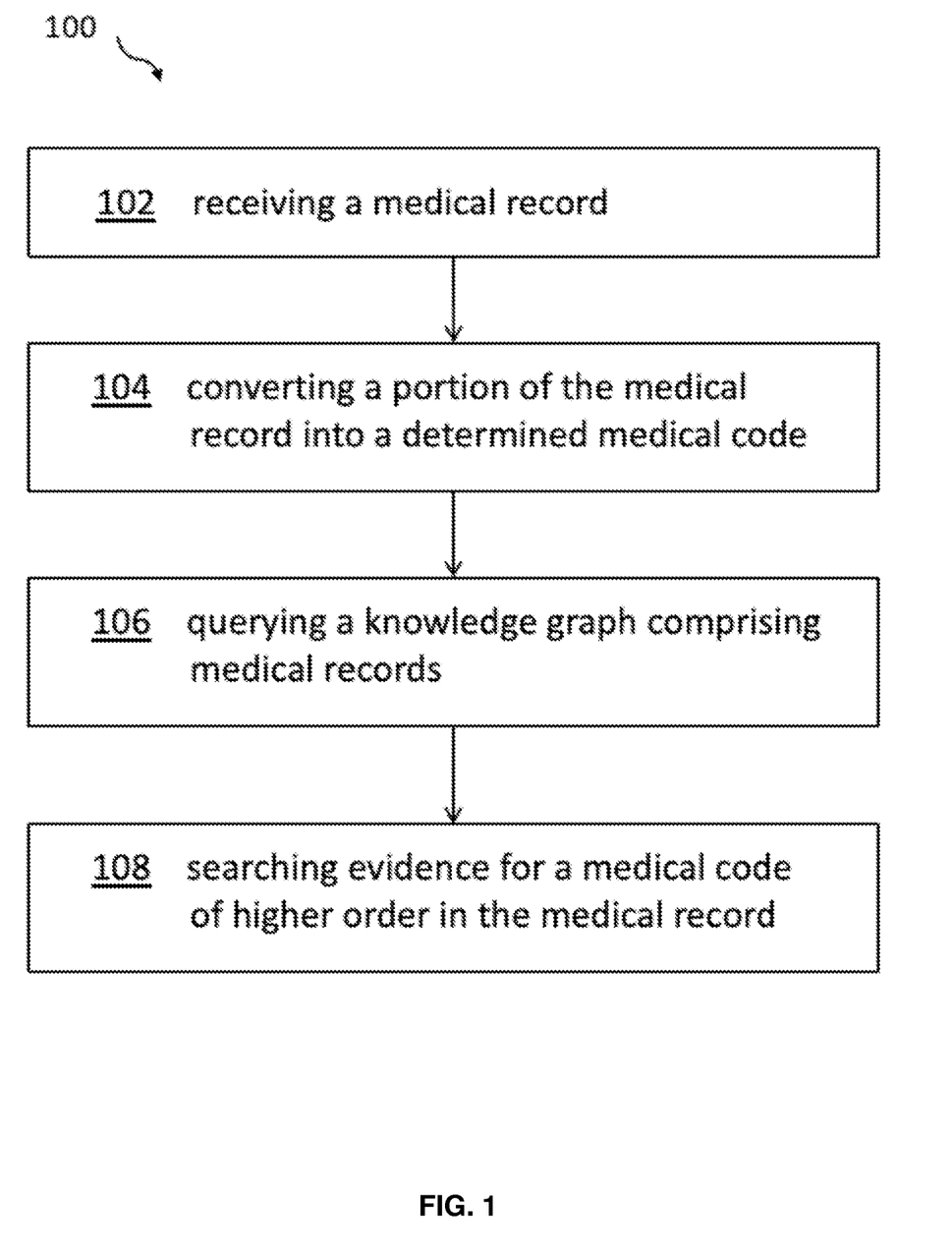
FIG. 1 shows a block diagram of an embodiment of the inventive computer-implemented method for augmenting medical coding.

FIG. 1 shows a block diagram of a preferred embodiment of the computer-implemented method 100 for augmenting medical coding. The method 100 comprises receiving, 102, a medical record—in particular at least one which may be determined as the selected medical record—in machine-readable text-form comprising at least one treatment. The treatment may be expressed as one or more natural language expressions or, already as a short character code, the main code, e.g., comprising three (ASCII) characters. The method 100 comprises also converting, 104, a portion of the medical record into a determined medical code. The conversion may be performed in two ways: (a) if the medical record already comprises a medical code indicating a treatment or a procedure, the identified medical code of the first length—e.g., three letters—may only be copied; (b) if the medical code cannot be determined as a code of the first length, the system underlying the proposed method uses individual expressions in the medical record and queries a knowledge graph for potential expressions relating to medical codes of the first length. These codes or this code are/is then used as the converted portion of the medical record.

Additionally, the method 100 comprises querying, 106, a knowledge graph comprising medical records—e.g., historic medical records with related correct medical codes and at least one coding catalog—for a medical code of higher order—in particular longer than three characters, e.g. 4 or 5 characters long—than the medical code of the first length relating to the determined medical code.

Last but not least, the method 100 comprises searching, 108, evidence for a medical code of higher order in the medical record by comparing at least a portion of clear text relating to a medical code of higher order with the medical record. The evidence may be found as an expression in the medical record which may also be found in the knowledge graph and which is related to the medical code of a first length determined before.

Figure 2:
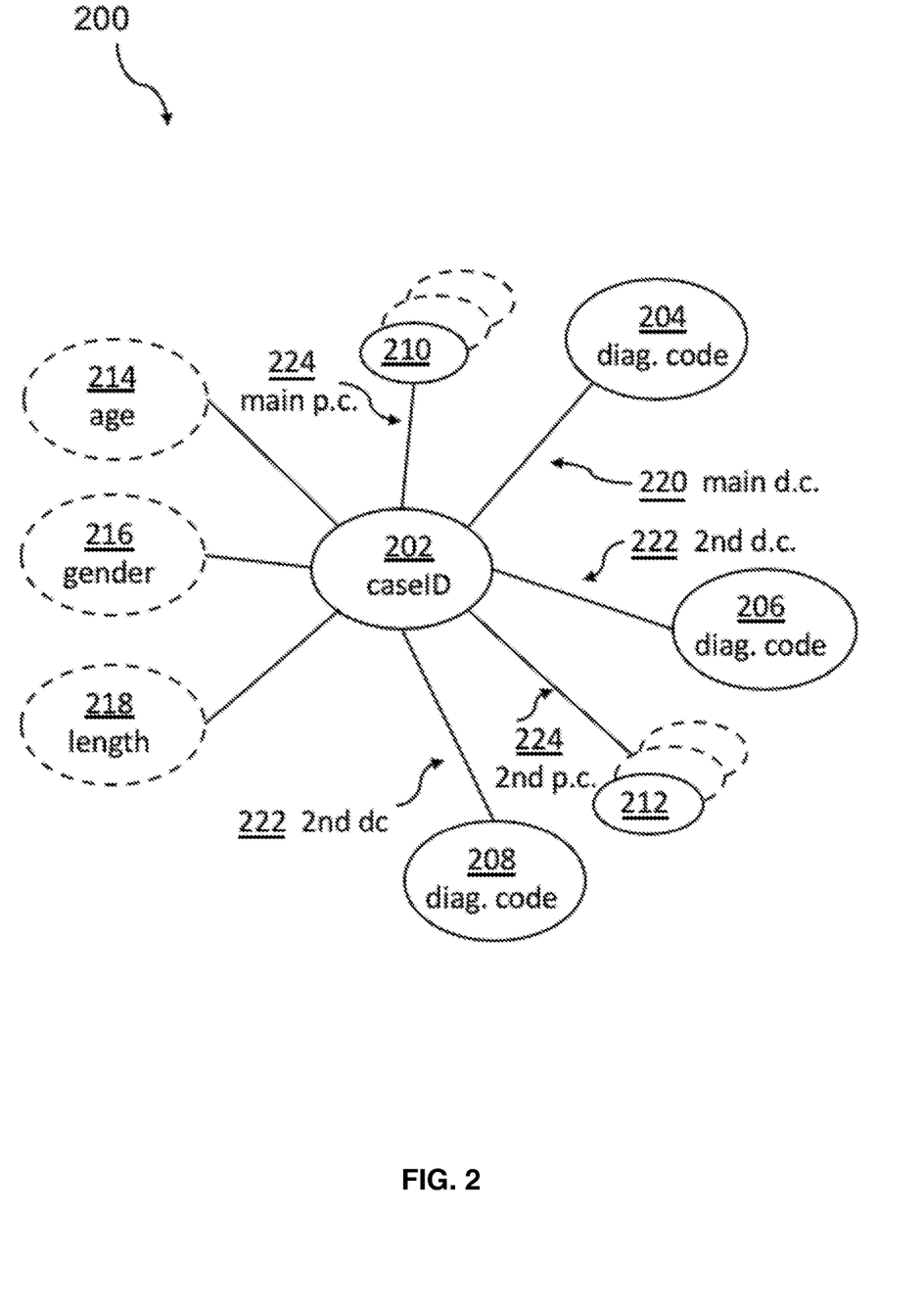
FIG. 2 shows a block diagram of an exemplary fraction of a knowledge graph supporting the here underlying concept.

FIG. 2 shows a block diagram 200 of an exemplary fraction—however, nevertheless representative part—of a knowledge graph supporting that underlying concept. In the center, the caseID 202 (case identifier for a specific medical case) is shown. Related to this is a diagnostic code 204 which typically has been identified by the first machine-learning based NLP system in which the diagnostic code 204 should have been identified from the digital image of a handwritten medical record. The edge 220 between the caseID node 202 and the diagnosis code 204 is shown as main diagnostic node as attribute of the edge 220. Similarly, the edge 222 may describe the diagnosis code as secondary diagnosis code 206, 208. Furthermore, the nodes 212 may be defined as secondary procedure codes. The same may apply to the node(s) 210 which may be defined by the edge 224 as main procedure code(s).

Additionally, other attributes of the patient, like age 214, gender 216 or length of stay 218 (and optionally additional patient attributes), can be linked via edges to the caseID 202.

Many of such a knowledge sub-graph cell (as just described) build the basis for a complete knowledge graph comprising information about many caseIDs enhanced by information from a catalog of diagnosis codes (e.g., ICD-10 codes) and procedural codes (e.g., OPS and/or CHOP codes) together with a set of rules (like the dependency rules codified in the DRG handbook).

Figure 3:
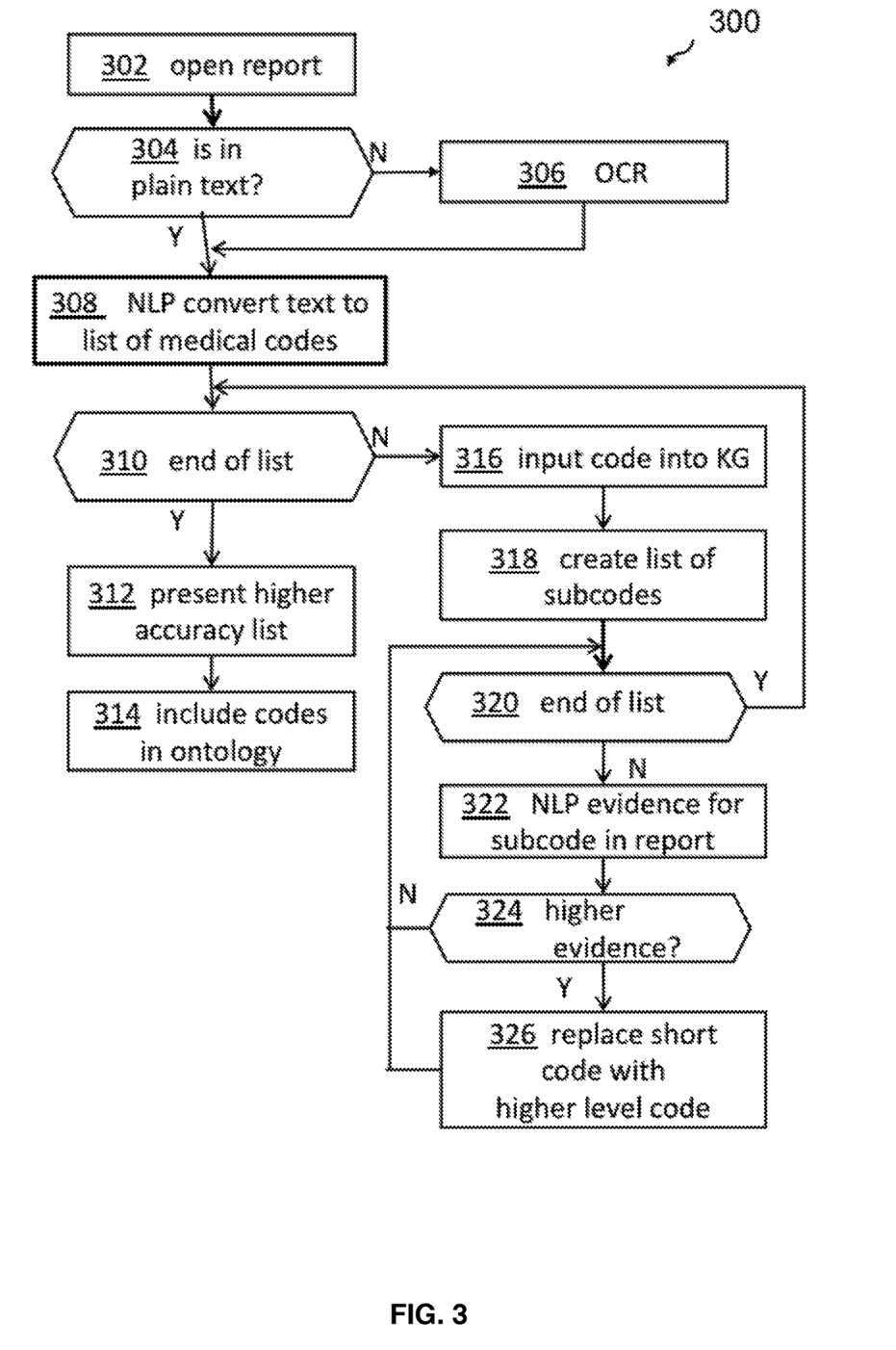
FIG. 3 shows an exemplary more implementation-near flowchart of the proposed concept.

FIG. 3 shows an exemplary more implementation-near flowchart 300 of the here proposed concept. The process starts, 302, with the opening of a new medical record, e.g., a surgery report, a discharge report or similar. Then, it is determined, 304, whether the medical record is available in machine-readable, e.g., plain text. If that is not the case—case "N"—the non-machine-readable medical record is converted, 306, into a machine-readable form, by either using an optical character recognition system (if the medical record is available in form of a digital image) or, by converting a PDF (portable document format) version of the medical record into a machine-readable form. Also other forms of converting a file into a machine-readable form are possible.

In both cases, a natural language processing system is used, 308, to convert the now machine-readable text into at least one, in particular, a list of medical (main) codes. The list may comprise ICD-10 and/or procedure codes. If the end of the list is not reached—case "N"—the ICD-10 code—in particular that of the first length is used as input into a knowledge graph, 316. The knowledge graph returns, 318, as search results codes (i.e., subcodes, i.e., child codes) which are codes with a higher degree of detail (if, e.g., a three digit ICD-10 code was found, or related four and five digit codes that are associated with the 3 digit code are returned). Additionally, a number of occurrences of that code in the knowledge graph case population is optionally also returned.

Also in this branch of the procedure, it is tested, 320, whether an end of the list is reached. If that is the case—case "Y"—the process returns to the next medical code of the first length, i.e., accesses and reads the next medical record. If the end of the list is not reached in the determination 320—case "N"—evidence is searched in the machine-readable form of the medical record using a natural language processing system, 322. The top of the list—i.e., with entries having an evidence value larger than a predefined threshold value—is then presented to a user for a final confirmation of the correct coding with the medical code of the second length. After a confirmation, the short medical code, i.e., the main code is replaced in the output coding list relating to the selected medical record by the longer medical code relating to a high degree of detail of the treatment procedure. It may be noted that the last two process steps are summarized in the flowchart as steps 324, 326.

If the end of the list has been reached in the determination 310 "end of list"—and alternatively to a user confirmation as part of the inner loop of the flowchart (the process on the right side of FIG. 3) entries in the list relating to the selected medical record are presented, 312—in particular those for which a high accuracy—i.e., higher evidence value—is assumed to a user for a confirmation. Finally, those codes that have been confirmed may then be included, 314, as codes into the ontology of the NLP system, allowing to reuse the newly gained knowledge—i.e., the pairing of an expression in the medical records and a medical (sub-) code for a next medical record which may be selected in the next run of the procedure.

Figure 4:
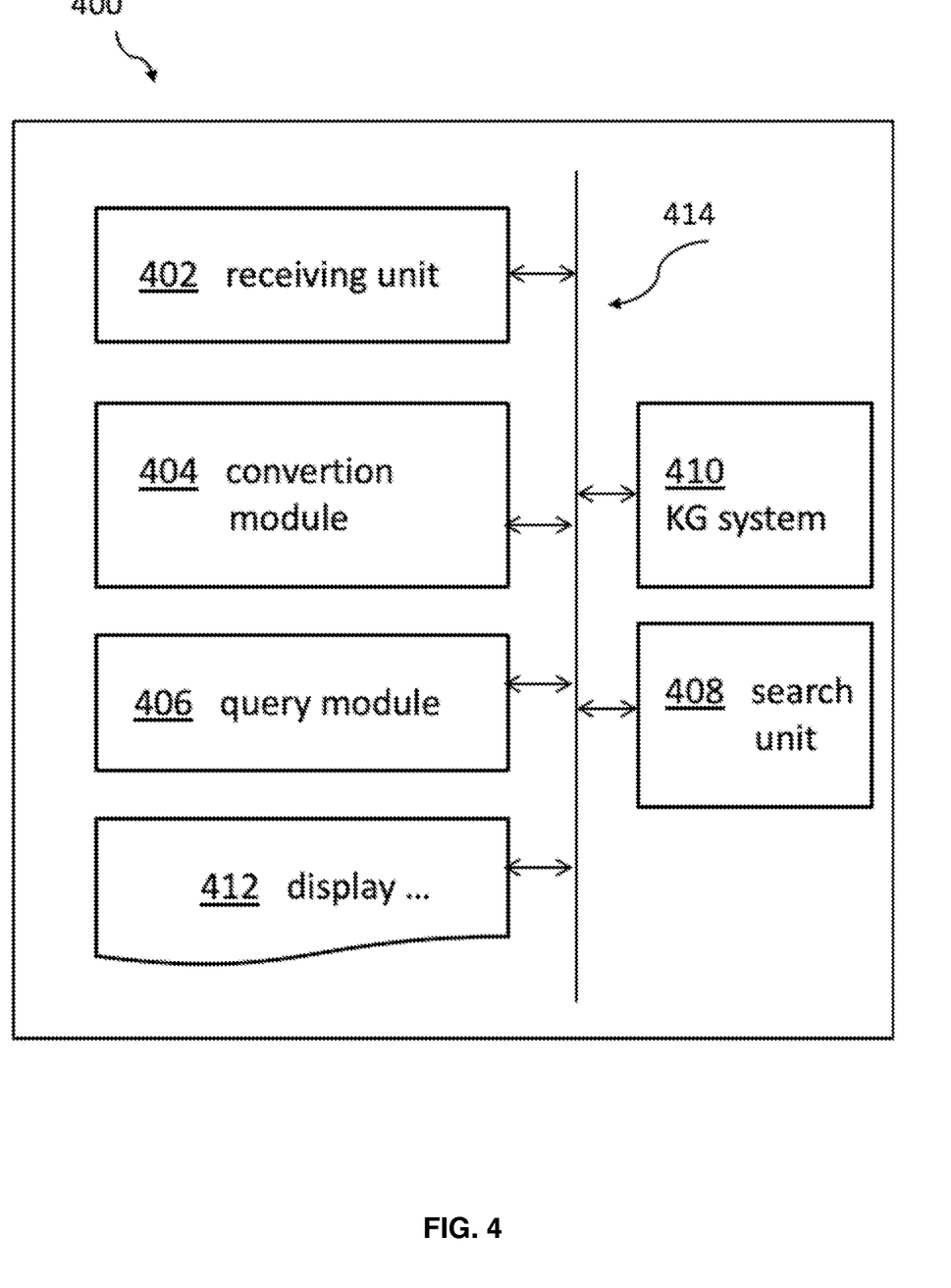
FIG. 4 shows a block diagram of an embodiment of the proposed system for augmenting medical coding.

For completeness reasons, FIG. 4 shows a block diagram of an embodiment of the proposed system 400 for augmenting medical coding. The coding system 400 comprises receiving means—in particular, a receiving unit 402—adapted for receiving a medical record (the selected one) in machine-readable text-form comprising at least one treatment, conversion means—in particular a conversion module 404—adapted for converting a portion of the medical record) into a determined medical code of a first length, query means—in particular, a query module 406—adapted for querying a knowledge graph or a knowledge graph system 410 comprising medical records and a coding catalog for a medical code of higher order than the medical code of the first length relating to the determined medical code, and search means—in particular, a search unit 408—adapted for searching evidence for a medical code of higher order in the medical record by comparing at least a portion of clear text relating to a medical code of higher order with the medical record. Additionally, a displaying and confirmation module 412 can also be part of the proposed system 400.

It may be noted that all modules, units or other functional blocks may be electrically connected for a signal exchange between the module and units and other functional blocks. This relates in particular to the receiving unit 402, the conversion module 404, the query module 406, displaying and confirmation module 412, the knowledge graph system 410, and the search unit 408. These functional blocks may be connected directly to each other of via a system internal bus system 414.

Figure 5:
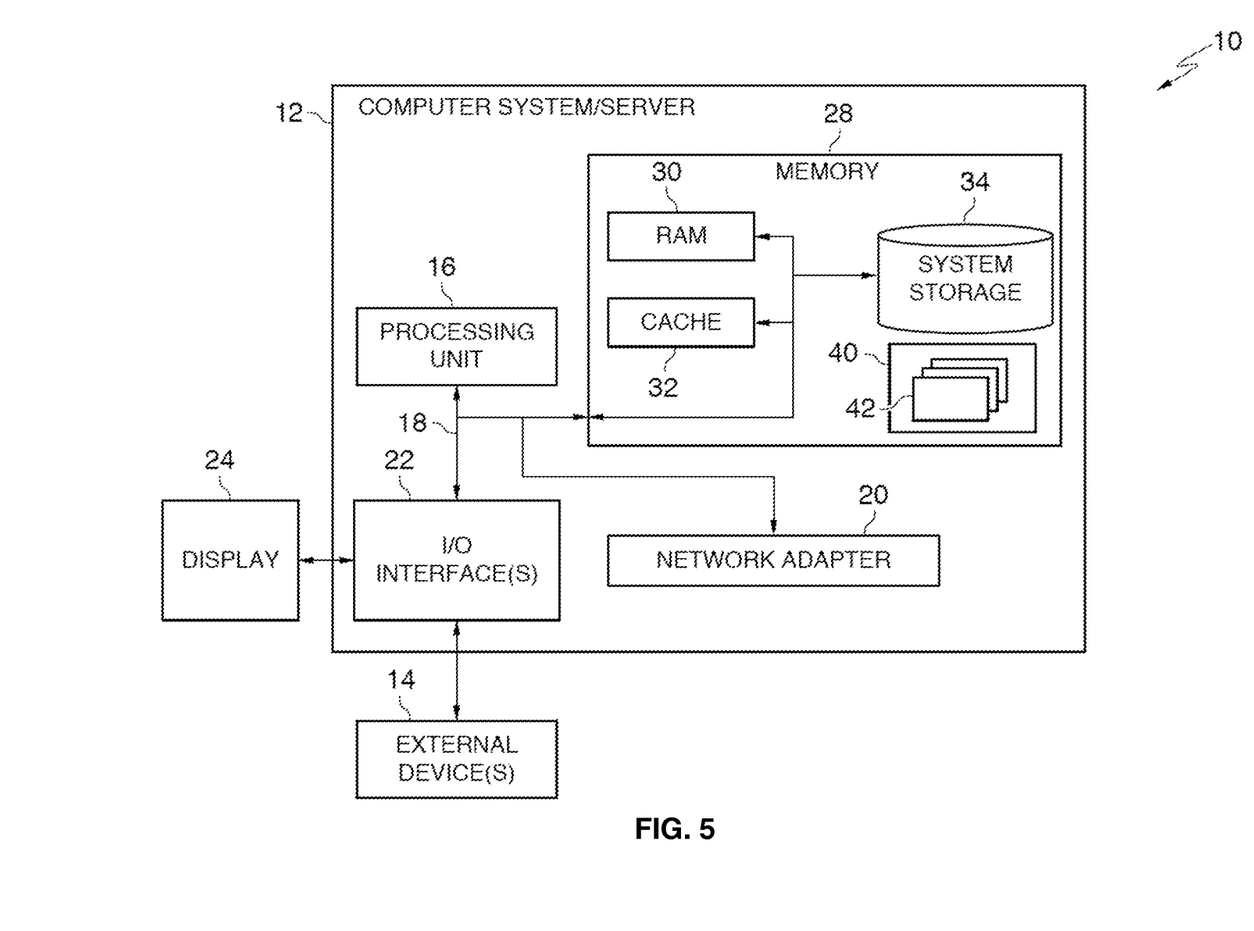
FIG. 5 depicts an exemplary block diagram depicting the hardware components of the disclosed system, in accordance with the exemplary embodiments.

FIG. 5 depicts a block diagram of devices in accordance with the exemplary embodiments. It should be appreciated that FIG. 5 provides only an illustration of one implementation and does not imply any limitations with regard to the environments in which different embodiments may be implemented. Many modifications to the depicted environment may be made.

Devices used herein may include one or more processors 02, one or more computer-readable RAMs 04, one or more computer-readable ROMs 06, one or more computer readable storage media 08, device drivers 12, read/write drive or interface 14, network adapter or interface 16, all interconnected over a communications fabric 18. Communications fabric 18 may be implemented with any architecture designed for passing data and/or control information between processors (such as microprocessors, communications and network processors, etc.), system memory, peripheral devices, and any other hardware components within a system.

One or more operating systems 10, and one or more application programs 11 are stored on one or more of the computer readable storage media 08 for execution by one or more of the processors 02 via one or more of the respective RAMs 04 (which typically include cache memory). In the illustrated embodiment, each of the computer readable storage media 08 may be a magnetic disk storage device of an internal hard drive, CD-ROM, DVD, memory stick, magnetic tape, magnetic disk, optical disk, a semiconductor storage device such as RAM, ROM, EPROM, flash memory or any other computer-readable tangible storage device that can store a computer program and digital information.

Devices used herein may also include a R/W drive or interface 14 to read from and write to one or more portable computer readable storage media 26. Application programs 11 on said devices may be stored on one or more of the portable computer readable storage media 26, read via the respective R/W drive or interface 14 and loaded into the respective computer readable storage media 08.

Devices used herein may also include a network adapter or interface 16, such as a TCP/IP adapter card or wireless communication adapter (such as a 4G wireless communication adapter using 01-DMA technology). Application programs 11 on said computing devices may be downloaded to the computing device from an external computer or external storage device via a network (for example, the Internet, a local area network or other wide area network or wireless network) and network adapter or interface 16. From the network adapter or interface 16, the programs may be loaded onto computer readable storage media 08. The network may comprise copper wires, optical fibers, wireless transmission, routers, firewalls, switches, gateway computers and/or edge servers.

Devices used herein may also include a display screen 20, a keyboard or keypad 22, and a computer mouse or touchpad 24. Device drivers 12 interface to display screen 20 for imaging, to keyboard or keypad 22, to computer mouse or touchpad 24, and/or to display screen 20 for pressure sensing of alphanumeric character entry and user selections. The device drivers 12, R/W drive or interface 14 and network adapter or interface 16 may comprise hardware and software (stored on computer readable storage media 08 and/or ROM 06).

The programs described herein are identified based upon the application for which they are implemented in a specific one of the exemplary embodiments. However, it should be appreciated that any particular program nomenclature herein is used merely for convenience, and thus the exemplary embodiments should not be limited to use solely in any specific application identified and/or implied by such nomenclature.

Based on the foregoing, a computer system, method, and computer program product have been disclosed. However, numerous modifications and substitutions can be made without deviating from the scope of the exemplary embodiments. Therefore, the exemplary embodiments have been disclosed by way of example and not limitation.

It is to be understood that although this disclosure includes a detailed description on cloud computing, implementation of the teachings recited herein are not limited to a cloud computing environment. Rather, the exemplary embodiments are capable of being implemented in conjunction with any other type of computing environment now known or later developed.

Cloud computing is a model of service delivery for enabling convenient, on-demand network access to a shared pool of configurable computing resources (e.g., networks, network bandwidth, servers, processing, memory, storage, applications, virtual machines, and services) that can be rapidly provisioned and released with minimal management effort or interaction with a provider of the service. This cloud model may include at least five characteristics, at least three service models, and at least four deployment models.

Characteristics are as follows:

On-demand self-service: a cloud consumer can unilaterally provision computing capabilities, such as server time and network storage, as needed automatically without requiring human interaction with the service's provider.

Broad network access: capabilities are available over a network and accessed through standard mechanisms that promote use by heterogeneous thin or thick client platforms (e.g., mobile phones, laptops, and PDAs).

Resource pooling: the provider's computing resources are pooled to serve multiple consumers using a multi-tenant model, with different physical and virtual resources dynamically assigned and reassigned according to demand There is a sense of location independence in that the consumer generally has no control or knowledge over the exact location of the provided resources but may be able to specify location at a higher level of abstraction (e.g., country, state, or data center).

Rapid elasticity: capabilities can be rapidly and elastically provisioned, in some cases automatically, to quickly scale out and rapidly released to quickly scale in. To the consumer, the capabilities available for provisioning often appear to be unlimited and can be purchased in any quantity at any time.

Measured service: cloud systems automatically control and optimize resource use by leveraging a metering capability at some level of abstraction appropriate to the type of service (e.g., storage, processing, bandwidth, and active user accounts). Resource usage can be monitored, controlled, and reported, providing transparency for both the provider and consumer of the utilized service.

Service Models are as follows:

Software as a Service (SaaS): the capability provided to the consumer is to use the provider's applications running on a cloud infrastructure. The applications are accessible from various client devices through a thin client interface such as a web browser (e.g., web-based e-mail). The consumer does not manage or control the underlying cloud infrastructure including network, servers, operating systems, storage, or even individual application capabilities, with the possible exception of limited user-specific application configuration settings.

Platform as a Service (PaaS): the capability provided to the consumer is to deploy onto the cloud infrastructure consumer-created or acquired applications created using programming languages and tools supported by the provider. The consumer does not manage or control the underlying cloud infrastructure including networks, servers, operating systems, or storage, but has control over the deployed applications and possibly application hosting environment configurations.

Infrastructure as a Service (IaaS): the capability provided to the consumer is to provision processing, storage, networks, and other fundamental computing resources where the consumer is able to deploy and run arbitrary software, which can include operating systems and applications. The consumer does not manage or control the underlying cloud infrastructure but has control over operating systems, storage, deployed applications, and possibly limited control of select networking components (e.g., host firewalls).

Deployment Models are as follows:

Private cloud: the cloud infrastructure is operated solely for an organization. It may be managed by the organization or a third party and may exist on-premises or off-premises.

Community cloud: the cloud infrastructure is shared by several organizations and supports a specific community that has shared concerns (e.g., mission, security requirements, policy, and compliance considerations). It may be managed by the organizations or a third party and may exist on-premises or off-premises.

Public cloud: the cloud infrastructure is made available to the general public or a large industry group and is owned by an organization selling cloud services.

Hybrid cloud: the cloud infrastructure is a composition of two or more clouds (private, community, or public) that remain unique entities but are bound together by standardized or proprietary technology that enables data and application portability (e.g., cloud bursting for load-balancing between clouds).

A cloud computing environment is service oriented with a focus on statelessness, low coupling, modularity, and semantic interoperability. At the heart of cloud computing is an infrastructure that includes a network of interconnected nodes.

Figure 6:
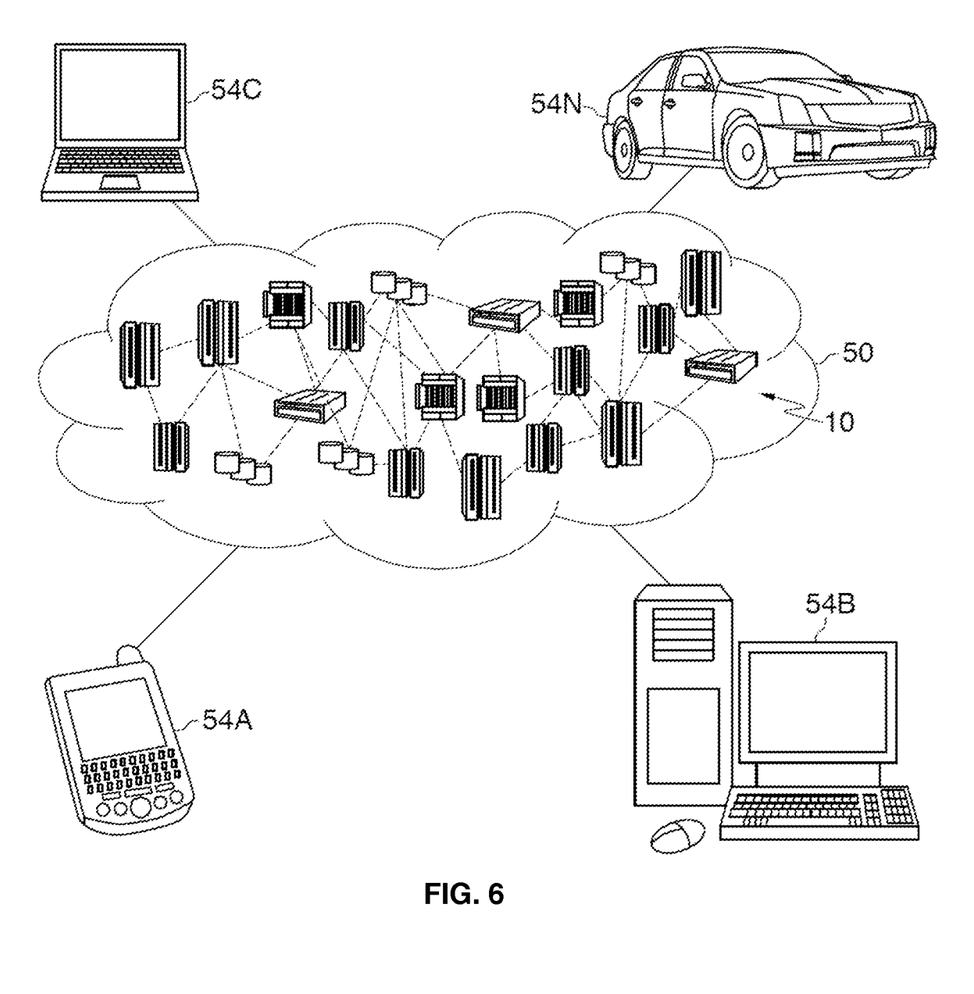
FIG. 6 depicts a cloud computing environment, in accordance with the exemplary embodiments.

Referring now to FIG. 6, illustrative cloud computing environment 50 is depicted. As shown, cloud computing environment 50 includes one or more cloud computing nodes 40 with which local computing devices used by cloud consumers, such as, for example, personal digital assistant (PDA) or cellular telephone 54A, desktop computer 54B, laptop computer 54C, and/or automobile computer system 54N may communicate. Nodes 40 may communicate with one another. They may be grouped (not shown) physically or virtually, in one or more networks, such as Private, Community, Public, or Hybrid clouds as described hereinabove, or a combination thereof. This allows cloud computing environment 50 to offer infrastructure, platforms and/or software as services for which a cloud consumer does not need to maintain resources on a local computing device. It is understood that the types of computing devices 54A-N shown in FIG. 6 are intended to be illustrative only and that computing nodes 40 and cloud computing environment 50 can communicate with any type of computerized device over any type of network and/or network addressable connection (e.g., using a web browser).

Figure 7:
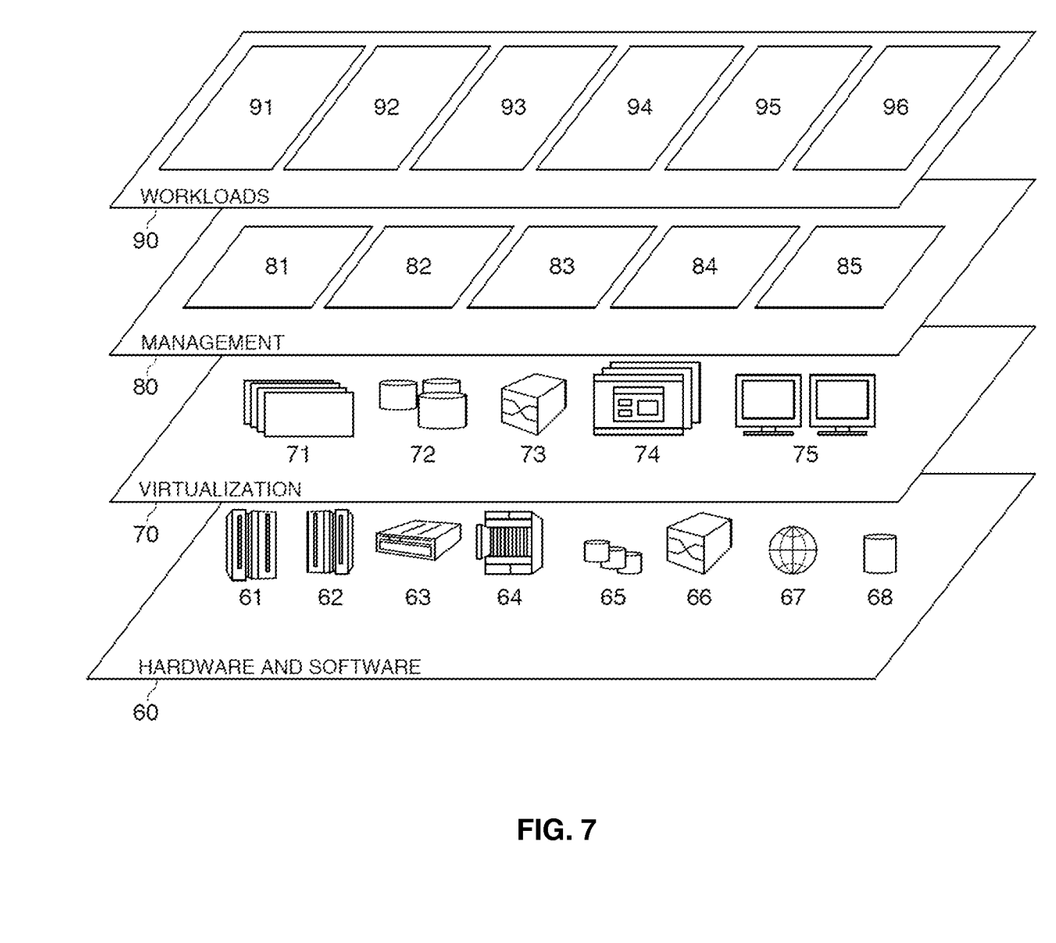
FIG. 7 depicts abstraction model layers, in accordance with the exemplary embodiments.

Referring now to FIG. 7, a set of functional abstraction layers provided by cloud computing environment 50 (FIG. 6) is shown. It should be understood in advance that the components, layers, and functions shown in FIG. 7 are intended to be illustrative only and the exemplary embodiments are not limited thereto. As depicted, the following layers and corresponding functions are provided:

Hardware and software layer 60 includes hardware and software components. Examples of hardware components include: mainframes 61; RISC (Reduced Instruction Set Computer) architecture based servers 62; servers 63; blade servers 64; storage devices 65; and networks and networking components 66. In some embodiments, software components include network application server software 67 and database software 68.

Virtualization layer 70 provides an abstraction layer from which the following examples of virtual entities may be provided: virtual servers 71; virtual storage 72; virtual networks 73, including virtual private networks; virtual applications and operating systems 74; and virtual clients 75.

In one example, management layer 80 may provide the functions described below. Resource provisioning 81 provides dynamic procurement of computing resources and other resources that are utilized to perform tasks within the cloud computing environment. Metering and Pricing 82 provide cost tracking as resources are utilized within the cloud computing environment, and billing or invoicing for consumption of these resources. In one example, these resources may include application software licenses. Security provides identity verification for cloud consumers and tasks, as well as protection for data and other resources. User portal 83 provides access to the cloud computing environment for consumers and system administrators. Service level management 84 provides cloud computing resource allocation and management such that required service levels are met. Service Level Agreement (SLA) planning and fulfillment 85 provide pre-arrangement for, and procurement of, cloud computing resources for which a future requirement is anticipated in accordance with an SLA.

Workloads layer 90 provides examples of functionality for which the cloud computing environment may be utilized. Examples of workloads and functions which may be provided from this layer include: mapping and navigation 91; software development and lifecycle management 92; virtual classroom education delivery 93; data analytics processing 94; transaction processing 95; and model augmented medical coding 96.

The descriptions of the various embodiments of the present invention have been presented for purposes of illustration, but are not intended to be exhaustive or limited to the embodiments disclosed. Many modifications and variations will be apparent to those of ordinary skills in the art without departing from the scope and spirit of the described embodiments. The terminology used herein was chosen to best explain the principles of the embodiments, the practical application or technical improvement over technologies found in the marketplace, or to enable others of ordinary skills in the art to understand the embodiments disclosed herein.

The present invention may be embodied as a system, a method, and/or a computer program product. The computer program product may include a computer readable storage medium (or media) having computer readable program instructions thereon for causing a processor to carry out aspects of the present invention.

The medium may be an electronic, magnetic, optical, electromagnetic, infrared or a semi-conductor system for a propagation medium. Examples of a computer-readable medium may include a semi-conductor or solid state memory, magnetic tape, a removable computer diskette, a random access memory (RAM), a read-only memory (ROM), a rigid magnetic disk and an optical disk. Current examples of optical disks include compact disk-read only memory (CD-ROM), compact disk-read/write (CD-R/W), DVD and Blu-Ray-Disk.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disk read-only memory (CD-ROM), a digital versatile disk (DVD), a memory stick, a floppy disk, a mechanically encoded device such as punchcards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, or either source code or object code written in any combination of one or more programming languages, including an object-oriented programming language such as Smalltalk, C++ or the like, and conventional procedural programming languages, such as the "C" programming language or similar programming languages. The computer readable program instructions may execute entirely on the user's computer, partly on the user's computer as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatuses, or another device to cause a series of operational steps to be performed on the computer, other programmable apparatus or other device to produce a computer implemented process, such that the instructions which execute on the computer, other programmable apparatuses, or another device implement the functions/acts specified in the flowchart and/or block diagram block or blocks.

The flowcharts and/or block diagrams in the figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or act or carry out combinations of special purpose hardware and computer instructions.

The terminology used herein is for the purpose of describing particular embodiments only and is not intended to limit the invention. As used herein, the singular forms "a", "an" and "the" are intended to include the plural forms as well, unless the context clearly indicates otherwise. It will further be understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

The corresponding structures, materials, acts, and equivalents of all means or steps plus function elements in the claims below are intended to include any structure, material, or act for performing the function in combination with other claimed elements, as specifically claimed. The description of the present invention has been presented for purposes of illustration and description, but is not intended to be exhaustive or limited to the invention in the form disclosed. Many modifications and variations will be apparent to those of ordinary skills in the art without departing from the scope and spirit of the invention. The embodiments are chosen and described in order to best explain the principles of the invention and the practical application, and to enable others of ordinary skills in the art to understand the invention for various embodiments with various modifications, as are suited to the particular use contemplated.

What is claimed is:

1. A computer-implemented method for augmenting medical coding, the method comprising:
   receiving a plurality of medical records wherein the medical records comprise at least one treatment;
   using a machine learning engine having a combination of a plurality of machine learning methods, including natural language processing (NLP), to build a relationship between a plurality of diagnosis codes and a plurality of procedural codes;
   using said machine learning engine to convert a portion of said plurality of medical records received into a machine readable first medical code using NLP;
   using said machine learning engine, querying a knowledge graph-comprising historical medical records and an associated procedural coding catalog for an output having records with at least one component that is the same as to that of said first medical code, generating a relationship between said output received and said first medical code to calculate a medical code of higher order;

using a training engine to search evidence in the medical record for the by comparing at least a portion of clear text the medical record; and providing a confidence score representing an estimation of a probability of a correctness of the generated second medical code, wherein the searching includes using a machine learning model to learn from a plurality of past coding decisions confirmed by a human user and integrating the evidence in the medical record into an ontology.

2. The method according to claim 1, further comprising converting the medical record into machine-readable text-form by optical character recognition.

3. The method according to claim 1, further comprising providing a confidence score representing an estimation of a probability of a correctness of the second medical code, wherein the confidence score for the second medical code is determined when the medical record comprises a synonym on abbreviation found in the knowledge graph during the query for the medical code of higher order.

4. The method according to claim 3, wherein said first medical code relates to a medical treatment further comprising:
displaying the determined confidence score; and
receiving a confirmation signal for replacing the first medical code with the second medical code.

5. The method according to claim 1, further comprising a surgery record or a discharge record for a patient.

6. The method according to claim 1, wherein the determined medical code is an ICD-10 code, OPS code, or a CHOP code.

7. The method according to claim 1, wherein the first medical code comprises three characters or wherein the second medical code comprise four or five characters.

8. The method according to claim 1, wherein querying a knowledge graph results in a list of medical codes of higher order.

9. The method according to claim 1, wherein converting a portion of the medical record into a determined medical code or searching for evidence for the second medical code in the medical record comprises the usage of a natural language processing system.

10. The method according to claim 3, further comprising including a confirmed medical code of higher order into the ontology used by a natural language processing system in order to expand an underlying set of dictionaries and their related relations in the knowledge graph.

11. The method according to claim 1:
wherein the medical records in the knowledge graph comprise medical codes associated with a main diagnosis and a secondary diagnosis,
wherein the main diagnosis and the secondary diagnosis are nodes in the knowledge graph,
wherein an association is represented as an edge between the medical code and one or more of the main diagnosis code or secondary diagnosis code, and
wherein the query to the knowledge graph also results in a likelihood of the association of the medical code of the received medical record with one or more of the main diagnosis code or the secondary diagnosis code.

12. A computer system for assigning medical codes, the computer system comprising:
one or more computer processors, one or more computer-readable storage media, and program instructions stored on the one or more of the computer-readable storage media for execution by at least one of the one or more processors capable of performing a method, the method comprising:

receiving a plurality of medical records wherein the medical records comprise at least one treatment;

using a machine learning engine having a combination of a plurality of machine learning methods, including natural language processing (NLP), to build a relationship between a plurality of diagnosis codes and a plurality of procedural codes;

using said machine learning engine to convert a portion of said plurality of medical records received into a machine readable first medical code using NLP;

using said machine learning engine, querying a knowledge graph-comprising historical medical records and an associated procedural coding catalog for an output of similar having records with at least one component that is the same as to that of said first medical code, generating a relationship between said output received and said first medical code to calculate a medical code of higher order;

using a training engine to search evidence in the medical record for the by comparing at least a portion of clear text the medical record; and providing a confidence score representing an estimation of a probability of a correctness of the generated second medical code, wherein the searching includes using a machine learning model to learn from a plurality of past coding decisions confirmed by a human user and integrating the evidence in the medical record into an ontology.

13. The coding system according to claim 12, further comprising converting the medical record into machine-readable text-form by optical character recognition.

14. The coding system according to claim 12 further comprising comparing at least a portion of clear text relating to the second medical code with the medical record wherein the confidence score for the second medical code is determined when the medical record comprises a synonym on abbreviation found in the knowledge graph during the query for the medical code of higher order.

15. The method according to claim 14, wherein said first medical code relates to a medical treatment further comprising:
displaying the determined confidence score; and
receiving a confirmation signal for replacing the first medical code with the second medical code.

16. The coding system according to claim 12, wherein the medical record comprises a surgery record or a discharge record for a patient.

17. The coding system according to claim 12, wherein the determined medical code is an ICD-10 code, OPS code, or a CHOP code.

18. The coding system according to claim 12, wherein the first medical code comprises three characters or wherein the second medical code comprise four or five characters.

19. A computer program product for assigning medical codes, the computer program product comprising:
one or more non-transitory computer-readable storage media and program instructions stored on the one or more non-transitory computer-readable storage media capable of performing a method, the method comprising:

receiving a plurality of medical records wherein the medical records comprise at least one treatment;

using a machine learning engine having using a combination of a plurality of machine learning methods, including natural language processing (NLP), to build a relationship between a plurality of diagnosis codes and a plurality of procedural codes;

using said machine learning engine to convert a portion of said plurality of medical records received into a machine readable first medical code using NLP;

using said machine learning engine, querying a knowledge graph-comprising historical medical records and an associated procedural coding catalog for an output having records with at least one component that is the same as to that of said first medical code, generating a relationship between said output received and said first medical code to calculate a medical code of higher order;

using a training engine to search evidence in the medical record for the by comparing at least a portion of clear text the medical record; and providing a confidence score representing an estimation of a probability of a correctness of the generated second medical code, wherein the searching includes using a machine learning model to learn from a plurality of past coding decisions confirmed by a human user and integrating the evidence in the medical record into an ontology.

* * * * *